United States Patent
Lin et al.

(12)

(10) Patent No.: US 6,303,380 B1
(45) Date of Patent: Oct. 16, 2001

(54) CONSTRUCTION OF RETROVIRAL PRODUCER CELLS FROM ADENOVIRAL AND RETROVIRAL VECTORS

(75) Inventors: Xinli Lin; Jordan J. N. Tang, both of Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/301,846

(22) Filed: Apr. 29, 1999

Related U.S. Application Data

(60) Provisional application No. 60/083,511, filed on Apr. 29, 1998.

(51) Int. Cl.$^7$ ............... C12N 5/10; C12N 15/861; C12N 15/867
(52) U.S. Cl. ............... 435/457; 435/320.1; 435/325; 435/357; 435/367; 435/372.3; 435/456
(58) Field of Search ............... 435/320.1, 366, 435/372, 372.3, 455, 456, 325, 357, 367, 457; 536/23.1, 23.2, 23.5

(56) References Cited

U.S. PATENT DOCUMENTS

| | | |
|---|---|---|
| 4,861,719 | 8/1989 | Miller . |
| 5,278,056 | 1/1994 | Bank et al. . |
| 5,449,614 | 9/1995 | Danos et al. . |
| 5,591,624 | 1/1997 | Barber et al. . |
| 5,691,177 * | 11/1997 | Guber et al. ............... 435/172.3 |
| 5,716,975 | 2/1998 | Bue-Valleskey et al. . |
| 5,719,137 | 2/1998 | Washburn et al. . |
| 5,731,284 | 3/1998 | Williams . |
| 5,731,354 | 3/1998 | Pruss . |
| 5,736,565 | 4/1998 | Ferrari . |
| 5,885,806 | 3/1999 | Dropulic et al. . |

FOREIGN PATENT DOCUMENTS

| | | |
|---|---|---|
| WO 96/33280 A1 | 10/1996 | (WO) . |
| WO 97/30169 A1 | 8/1997 | (WO) . |
| WO 98/13499 A2 | 4/1998 | (WO) . |
| WO 98/13510 A1 | 4/1998 | (WO) . |

OTHER PUBLICATIONS

Adam, et al., "Internal initiation of translation in retroviral vectors carrying picornavirus 5' nontranslated regions," *J Virol.* 65(9):4985–90 (1991).

Afione, et al., "Gene therapy vectors as drug delivery systems," *Clin Pharmacokinet.* 28(3):181–9 (1995).

Bett, et al., "An efficient and flexible system for construction of adenovirus vectors with insertions or deletions in early regions 1 and 3," *Proc Natl Acad Sci U S A.* 91(19):8802–6 (1994).

Bett, et al., "Packaging capacity and stability of human adenovirus type 5 vectors." *J Virol.* Oct. 1993;67(10):5911–21.

Bilbao, et al., "Adenoviral/retroviral vector chimeras: a novel strategy to achieve high–efficiency stable transduction in vivo," *FASEB J.* 11(8):624–34 (1997).

Blaese, et al., "Vectors in cancer therapy: how will they deliver?" *Cancer Gene Ther.* 2(4):291–7 (1995).

Blaese, et al., "The ADA Human Gene Therapy Clinical Protocol," *Hum Gene Ther* 1:327–329 (1990).

Bordignon, et al., "Gene therapy in peripheral blood lymphocytes and bone marrow for ADA—immunodeficient patients," *Science.* 270(5235):470–5 (1995).

Bramson, et al., "The use of adenoviral vectors for gene therapy and gene transfer in vivo," *Curr Opin Biotechnol.* 6(5):590–5 (1995).

Chuah, et al., "Development and analysis of retroviral vectors expressing human factor VIII as a potential gene therapy for hemophilia A," *Hum Gene Ther.* 6(11):1363–77 (1995).

Colledge, et al., "Cystic fibrosis gene therapy," *Br Med Bull.* 51(1):82–90 (1995).

Cosset, et al. "Targeting retrovirus entry," *Gene Therapy* 3:946–956 (1996).

Cournoyer & Caskey, "Gene therapy of the immune system," *Annu. Rev. Immunol.* 11:297–329 (1993).

Culver, et al., "In Vivo Gene Transfer with Retroviral Vector–Producer Cells for Treatment of Experimental Brain Tumors," *Science* 256:1550–1552 (1992).

Felsenstein, et al., "Expression of the gag–pol fusion protein of Moloney murine leukemia virus without gag protein does not induce virion formation of proteolytic processing," *J Virol.* 62(6):2179–82 (1988).

Feng, et al., "Stable in vivo gene transduction via a novel adenoviral/retroviral chimeric vector," *Nat Biotechnol.* 15(9):866–70 (1997).

(List continued on next page.)

*Primary Examiner*—Robert A. Schwartzman
(74) *Attorney, Agent, or Firm*—Holland & Knight LLP

(57) ABSTRACT

A combination of adenoviral and retroviral vectors used to construct second generation packaging cells that deliver marker genes to target cells is described. A vector based upon Moloney murine leukemia virus (MLV) was used to deliver marker genes, and an adenovirus-based delivery system was used to deliver MLV structural genes (gagpol and env) to cultured cells. The procedure transformed the cells into new retroviral producer cells, which generate replication-incompetent retroviral particles in the culture supernatant for transferring marker genes to target cells. The titer of the retroviral-containing supernatant generated from the second generation producer cells reached above 105 cfu/ml which is comparable to the MLV-based producer cell lines currently used in human gene therapy trials. The vector and procedures are adaptable for experimental human gene therapy in which the new producer cells are transplanted into patients for continuous gene transfer.

12 Claims, 3 Drawing Sheets

OTHER PUBLICATIONS

Gartner & Popovic, "Virus Isolation and production," In *Techniques in HIV Research*, (Aldovini A, and Walker BD (eds)), pp. 53–70, Stockton Press, 1990.

Graham & Prevec, "Manipulation of Adenovisrus Vectors" in *Methods in Molecular Biology, Vol. 7: Gene Transfer and Expression Protocols*, (Murray EJ (ed.)), pp 109–128, Humana Press, Inc.:Clifton, NJ, 1991.

Graham & Van Der Eb, "A new technique for the assay of infectivity of human adenovirus 5 DNA," *Virology.* 52(2):456–67 (1973).

Grossman, et al., "Successful ex vivo gene therapy directed to liver in a patient with *Familial hypercholesterolaemia*, " *Nat Genet.* 6(4):335–41 (1994).

Hitt, et al., "Construction and propagation of human adenovirus vectors," In *Cell Biology: A Laboratory Handbook*, pp. 479–490, Academic Press:NY, 1994.

Jang, et al., "Cancer chemopreventive activity of resveratol, a natural product derived from grapes," *Science* 275:218–220 (1997).

Lin, et al., "A new retrovirus–based in vivo gene delivery strategy" Nov. 29–30, 1994, Washington, D.C.

Markowitz, et al., "A safe packaging line for gene transer: separating viral genes on two different plasmids," *J Virol.* 62(4):1120–4 (1988).

Markowitz, et al., "Retroviral gene transfer using safe and efficient packaging cell lines," *Ann N Y Acad Sci.* 612:407–14 (1990).

Miller & Verma, "Two base changes restore infectivity to a noninfectious molecular clone of Moloney murine leukemia virus (pMLV–1)," *J Virol.* 49(1):214–22 (1984).

Miller & Vile, "Targeted vectors for gene therapy," *FASEB J.* 9:190–199 (1995).

Miller, et al., "Redesign of retrovirus packaging cell lines to avoid recombination leading to helper virus production," *Mol Cell Biol.* 6(8):2895–902 (1986).

Miller, et al., "Use of retroviral vectors for gene transfer and expression," *Methods Enzymol.* 217:581–99 (1993).

Morgan, et al., "Human gene therapy," *Annu Rev Biochem.* 62:191–217 (1993).

Mulligan, et al., "The basic science of gene therapy," *Science* 260:926–932 (1993).

Noguiez–Hellin, et al., "Plasmoviruses: nonviral/viral vectors for gene therapy," *Proc Natl Acad Sci U S A.* 93:(9):4175–80 (1996).

Parnetti, et al., "Cognitive enhancement therapy for Alzheimer's Disease," *Drugs* 53:752–768 (1997).

Popovic, et al., "Detection, isolation, and continuous production of cytopathic retroviruses (HTLV–III) from patients with AIDS and pre–AIDS," *Science*, 224(4648):497–500 (1984).

Rettinger, et al., "Liver–directed gene therapy: quantitative evaluation of promoter elements by using in vivo retroviral transduction," *Proc Natl Acad Sci U S A.* 91(4):1460–4 (1994).

Rother, et al. "A novel mechanism of retrovirus inactivation in human serum mediated by anti–alpha–galactosyl natural antibody," *J Exp Med.* 182(5):1345–55 (1995).

Salmons, et al., "Construction of retroviral vectors for targeted delivery and expression of therapeutic genes," *Leukemia.* 9 Suppl 1:S53–60 (1995).

Savard, et al., "Defective herpes simplex virus type 1 vectors harboring gag, pol, and env genes can be used to rescue defective retrovirus vectors," *J Virol.* 71(5):4111–7 (1997).

Smith, "Viral vectors in gene therapy," *Annu Rev Microbiol.* 49:807–38 (1995).

Smith, et al., "Gene therapy in heart disease," *Adv Exp Med Biol.* 369:79–88 (1995).

Thal, "Potential prevention strategies for Alzheimer disease," *Alzheimer Disease and Associated Disorders* 10(Suppl 1):6–8 (1996).

Vile, et al., "Retroviruses as vectors," *Br Med Bull.* 51(1):12–30 (1995).

Wei et al., "Construction and isolation of a transmissible retrovirus containing the src gene of Harvey murine sarcoma virus and the thymidine kinase gene of herpes simplex virus type 1," *J Virol.* 39(3):935–44 (1981).

Welsh, et al., "Human serum lyses RNA tumor viruses," *Nature* 257:612–614 (1975).

Wilson, "Adenoviruses as gene–delivery vehicles," *N Engl J Med.* 334(18):1185–7 (1996).

Yoshida, et al., "Adenovirus–mediated inducible gene expression through tetracycline–controllable transactivator with nuclear localization signal," *Biochem Biophys Res Commun.* 230(2):426–30 (1997).

Yoshida, et al., "VSV–G–pseudotyped retroviral packaging through adenovirus–mediated inducible gene expression," *Biochem Biophys Res Commun.* 232(2):379–82 (1997).

Yu, et al., "Progress towards gene therapy for HIV infection," *Gene Ther.* 1(1):13–26 (1994).

Zabner, et al., "Repeat administration of an adenovirus vector encoding cystic fibrosis transmembrane conductance regulator to the nasal epithelium of patients with cystic fibrosis," *J Clin Invest.* 97(6):1504–11 (1996).

* cited by examiner

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:

```
<223> OTHER INFORMATION: Description of Artificial Sequence: internal
      primer of pLN- forward primer
<221> NAME/KEY: misc_feature
<222> LOCATION: (1)..(30)
<223> OTHER INFORMATION: oligonucleotide primer

<400> SEQUENCE: 1
cccgattcgc agcgcatcgc cttctatcgc                              30

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: internal
      primer of pLN- reverse primer
<221> NAME/KEY: misc_feature
<222> LOCATION: (1)..(20)
<223> OTHER INFORMATION: oligonucleotide primer

<400> SEQUENCE: 2
gcagaggaga ccctcccaag                                         20

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence:
      oligonucleotide primer- CAM3P1
<221> NAME/KEY: misc_feature
<222> LOCATION: (1)..(54)
<223> OTHER INFORMATION: oligonucleotide primer
<221> NAME/KEY: mutation
<222> LOCATION: (44)
<223> OTHER INFORMATION: c changed to t
<221> NAME/KEY: misc_feature
<222> LOCATION: (1)..(6)
<223> OTHER INFORMATION: installed HpaI site

<400> SEQUENCE: 3
gttaaccagg gaccaccgac ccaccaccgg gaggtaagct gggttgcagc atcg    54

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer- CAM3P2
<221> NAME/KEY: misc_feature
<222> LOCATION: (1)..(21)
<223> OTHER INFORMATION: oligonucleotide primer
<221> NAME/KEY: misc_feature
<222> LOCATION: (1)..(6)
<223> OTHER INFORMATION: original PstI site

<400> SEQUENCE: 4
ctgcagagca gaaggtaacc c                                       21
```

CONSTRUCTION OF RETROVIRAL PRODUCER CELLS FROM ADENOVIRAL AND RETROVIRAL VECTORS

CROSS-REFERENCE TO RELATED APPLICATIONS

Priority is claimed to U.S. Provisional application Serial No. 60/083,511, filed Apr. 29, 1998.

BACKGROUND OF THE INVENTION

The present invention is in the field of retroviral vectors for gene therapy.

Recent progress in human genetics, especially in human genome research and gene transfer techniques, has brought gene therapy closer to clinical reality. Experimental human gene therapy has enjoyed some successes in the treatment of genetic defects, including adenosine deaminase deficiency, (Blaese R M, et al. Sciene 1995; 270: 470–474; Blaese R M, et al. Hum Gene Ther 1990; 1: 327–329, Bordignon C, et al. Science 1995; 270: 470–474) familial hypercholesterolemia, (Grossman M, et al. Nature Genet 1994; 6: 335–341) hemophilia, (Chuah M K L, et al. Hum Gene Ther 1995, 6: 1363–1377) and cystic fibrosis, (Colledge W H, et al. Brit Med Bull 1995; 51: 82–90) and acquired diseases such as cancer (Blaese R M, et al. Cancer Gene Ther 1995; 2: 291–297), heart disease (Smith L C, et al. Adv Exp Med Biol 1995; 369: 77–88), kidney disease (Smith L C, et al. Adv Exp Med Biol 1995; 369: 77–88), and acquired immunodeficiency syndrome (Yu M, et al. Gene Ther 1994; 1: 13–26).

At present, the primary limitation in the use of gene therapy to treat human disease is the ineffectiveness of gene delivery methods. Among several types of gene delivery systems for human gene therapy in clinical trials, Moloney murine leukemia virus (MLV) based vectors are the most widely used (Afione S A, et al. Clin Pharmacokinet 1995; 28: 181–189; Morgan R A, et al. Annu Rev Biochem 1993; 62: 191–217; Smith A E. Annu Rev Microbiol 1995; 49: 807–838, Vile R G, et al. Brit Med Bull 1995; 51: 12–30). MLV-based vectors offer highly efficient chromosome integration; thus, the therapeutic genes are transmitted to the progeny cells. However, MLV-based gene delivery methods are largely limited to ex vivo protocols, (Blaese R M, et al. Science 1995; 270: 470–474; Blaese R M, et al. Hum Gene Ther 1990; 1: 327–329; Bordignon C, et al. Science 1995; 270: 470–474; Grossman M, et al. Nature Genet 1994; 6: 335–341; Chuah M K L, et al. Hum Gene Ther 1995; 6: 1363–1377) in which the target cells are removed from the patient to receive therapeutic genes from the MLV vectors in vitro. Then the transduced cells are selected, expanded and reimplanted in the patient. The ex vivo procedure is cumbersome and costly, and in most cases, it can transduce only a small fraction of the target cell population (Rettinger S D, et al. Proc Natl Acad Sci USA 1994; 91: 1460–1464; Salmons B, et al. Leukemia 1995; 1: S53–S60). More efficient gene delivery protocols need to be developed, for advancing gene therapy to routine clinical practice.

In vivo gene transfer is conceptually attractive and potentially can be more efficient than the ex vivo procedure. However, due to limited titer (Vile R G, et al. Brit Med Bull 1995; 51: 12–30) and short half life at body temperature, direct administration of retroviral vectors into patients is limited in its applicability. Another alternative is to introduce producer cells directly into patients. In this scenario, gene transfer may continue in vivo for the duration of the life span of the implanted producer cells. Gene therapy using MLV-based producer cells to treat brain tumors (Culver K W, et al. Science 1992; 256: 1550–1552) has been carried out in clinical trials, but no clear clinical benefit has been reported Murine producer cells are rapidly inactivated in human serum, (Rother R P, et al J Exp Med 1995; 182: 1345–1355; Welsh R M, et al. Nature 1975; 257:612–614) thus, the lack of success in this case is not surprising. Implanting established human producer cell lines, however, risks the introduction of malignancy to the recipient. For these reasons, the conversion of human primary cells into producer cells has been proposed (Welsh R M, et al. Human serum lyses RNA tumor viruses. Nature 1975; 257:612–614). The primary cell-converted "producer cells" do not have the drawbacks discussed above yet they have the advantages of in vivo gene delivery.

Accordingly it is an object of the present invention to provide a method for gene delivery

SUMMARY OF THE INVENTION

A combination of adenoviral and retroviral vectors used to construct second generation packaging cells that deliver marker genes to target cells is described. A vector based upon Moloney murine leukemia virus (MLV) was used to deliver marker genes, and an adenovirus-based delivery system was used to deliver MLV structural genes (gagpol and env) to cultured cells. The procedure transformed the cells into new retroviral producer cells, which generate replication-incompetent retrovirat particles in the culture supernatant for transferring marker genes to target cells. The titer of the retroviral-containing supernatant generated from the second generation producer cells reached above $10^5$ cfu/ml, which is comparable to the MLV-based producer cell lines currently used in human gene therapy trials. Additional adenoviral/MLV-based vectors were constructed with increased safety, by replacing the 5'-LTR down to the primer binding site in pPAM3 and replacing it with a CMV promoter Another viral vector system was developed based on adenovirus and HIV. Adenoviral vectors for delivering HIV-1 gagpol genes and marker genes in a lentivurs construct were made.

The examples demonstrate the construction of these vectors as well as delivery and expression of the thymidine kinase gene and killing of tumors in mice following gancyclovir administration. The vectors and procedures are adaptable for human gene therapy in which the new producer cells are transplanted into patients for continuous gene transfer.

BRIEF DESCRIPTION OF THE DRAWINGS

FIG. 3A, pCA14-AR8.2, which is an adenovirus vector that delivers HIV-gagpol gene under the control of a CMV promoter, is derived from vector pCMV-ΔR8.2. FIG. 3B, adenovirus vector pΔE1A-v653-RSN, which contains HIV-based vector sequences, delivers NEO-marker gene, is derived from v653-RSN. FIG. 3C, pΔE1A-v653-GFP is the same as B. except that a CMV-GFP construct has been used to replace the SL3-NEO. 1 u, 9.8 u, map unit of adenovirus Ad-5.

FIG. 4A shows the construction of vector Lxpsp-HyTK. The unique restriction sites, XhoI and BamHI, are shown. FIG. 4B shows the dual expression vector pL-HyTK-mGM-CSF.

DETAILED DESCRIPTION OF THE INVENTION

Figure 1:
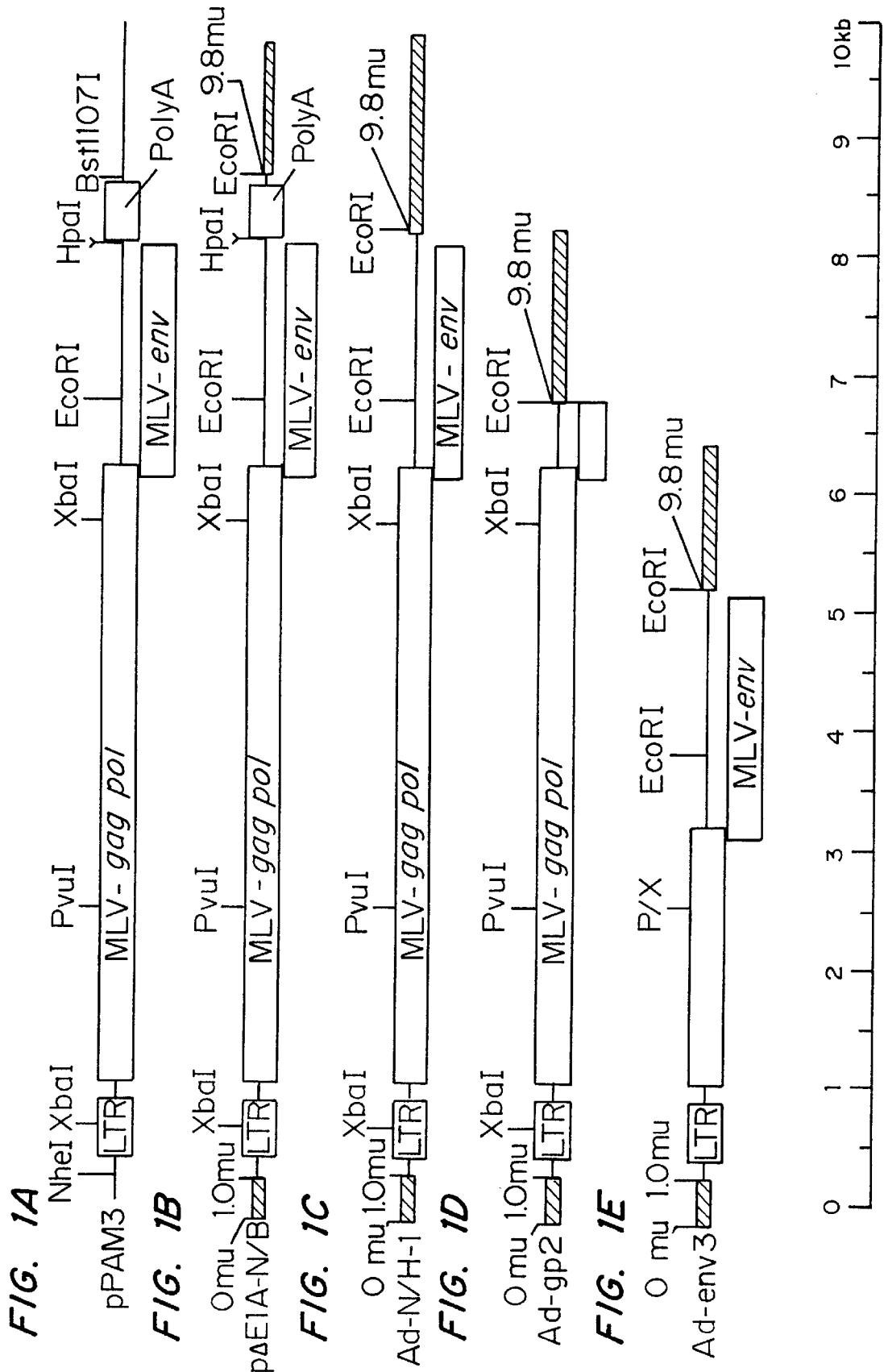
FIGS. 1A–1E are schematics of recombinant adenovirus gene constructs. From top to bottom, the constructs are: a) pPAM3, the parental MLV vector; b) pΔE1A-N/B, which contains the gagpol/env genes and a polyadenylation signal; c) Ad-N/H-1 which contains the gagpol/env genes and not a polyadenylation signal; d) Ad-gp2, which contains the MLV gag-pol genes; and e) Ad-env3, which contains the MLV env gene. mu is a map unit of adenovirus Ad-5.

To be converted to producer cells, human primary cells must acquire the therapeutic or marker gene and MLV structural genes gag, pol, and env. The former are delivered by a conventional MLV-based vector while the latter are delivered by adenoviral vectors. Different existing gene delivery systems are combined to produce new, and possibly more powerful, gene delivery constructs.

An experimental model is described that establishes that the described gene transfer procedure is technically feasible at the cellular level. The use of adenoviral vectors to transfer MLV packaging genes to establish cell lines and primary cells is described. Adenoviral vectors are an attractive choice for the transfer of MLV gag-pol-env genes into target cells since they have proven gene transfer efficiency and can accommodate a large insert. The transferred structural genes are expressed by the new producer cells, and the MLV particles are apparently assembled with packaged marker genes, which are capable of transducing new target cells. Thus the adenoviral vectors transduce naive cells into transient packaging cells. The titer of the new packaging cells reaches above $10^5$ cfu/ml, which is comparable to MLV packaging cell lines currently used in the ex vivo procedures.

Experiments tested the current vectors under different conditions. The adenoviral vectors carrying MLV structural genes were able to rescue two different MLV-markers (pLN and pLNPOZ) in three different cells lines (NIH 3T3 Hela, and H9). The pools of retroviruses transduced cells were also tested for adenoviral infection. This method is expected to produce lower titers but it is nevertheless a closer simulation for certain clinical applications, in which primary cells are first transduced with retroviral vectors, selected, then infected with adenoviral vectors. The results show that the vectors work reasonably well even with this rapid procedure. Moreover, co-infection by both retroviral and adenoviral vectors without selection also works. These results show that the vectors are reliable even under less than optimal condition. Finally, since the genes transferred from the adenoviral vectors are not chromosome-integrated, the decline of titers from later cell generations was tested. The data suggests that the decline of titers from the constructed producer cells was reasonably slow over time in further culturing.

The conversion of target cells into retroviral producer cells may be accomplished by different methods in which the MLV structural genes and the marker genes are transferred separately. The idea was first reported using a combination of MLV and HIV-based gene delivery to construct new packaging cells. (Lin X, et al. "Technological Advances for Gene Therapy" Nov. 29–30, 1994, Washington, D.C.) Noguiez-Hellin et al. have reported that by engineering MLV gagpol and env genes separately into a single plasmid, which is called plasmovirus, they can transform target cells into retroviral packaging cells by plasmid transfection. (Noguiez-Hellin P, et al. *Proc Natl Acad Sci USA*. 1996: 93: 4175–4180.) Recently, Savard et al. have reported the use of defective herpes simplex virus (Savard N. et al. *J Virol* 1997; 71: 4111–4117.) to deliver MLV structural genes, and demonstrated that the recombinant herpes virus can rescue defective retrovirus vectors in a permanent cell line. The use of adenoviruses to deliver both MLV structural genes and MLV vectors has been reported. (Bilbao G., et al *FASAB J* 1997; 11: 624–634. Feng M, et al. *Nature Biotechnol* 1997; 15: 866–870.) These authors also observed the secondary, permanent gene transfer in an in vitro and in vivo model after the primary adenoviral infection. In addition, tetracycline-controllable transactivator has been used to drive the expression of vesicular stomatitis virus G-protein (VSV-G) and MLV gag-pol in adenovirus vectors. (Yoshida Y, et al. *Biochem Biophys Res Commun* 1997; 232: 379–382. Yoshida Y. et al. *Biochem Biophys Res Commun* 1997; 230: 426–430.) These adenoviral vectors have been used to rescue retrovirat vectors, and results in production of high titer VSV-G-pseudotyped retroviruses in the supernatants.

The new producer cells transduced by adenoviral and retroviral vectors from primary cells may be introduced into patients to deliver therapeutic genes to target cells in vivo. Such a protocol has the advantage of a continuing in vivo gene transfer over the lifetime of the 'producer cell'. This is also a safe procedure because both MLV and adenovirus-based gene delivery has been widely used in human gene therapy clinical trials. (Blaese R M, et al. *Science* 1995; 270: 470–474. Blaese R M, et al. *Hum Gene Ther* 1990; 1: 327–329. Bordignon C, et al *Science* 1995; 270: 470–474. Grossman M, et, al. *Nature Genet* 1994; 6: 335–341. Chuah M K L, et al. *Hum Gene Ther* 1995; 6: 1363–1377. Bramson J L, et al. *Curr Opin Biotechnol* 1995; 6: 590–595. Wilson J M. *Molec Med* 1996; 334: 1185–1187. Zabner J, et al. *J Clin Invest* 1996; 97: 1504–1511.) Also, since long term survival of the producer cells in a patient is not essential in this method, then, unlike the ex vivo protocol, the producer cells need not necessarily be from the same patient. Thus there is potential to develop industrial scale universal therapeutic producer cells to treat many patients with similar defects.

The present invention is further described by the following non-limiting examples.

EXAMPLES

Materials and Methods

Adenoviral Vector Construction

Four adenovirus vectors (FIG. 1) were constructed from adenoviral vector pΔE1Asp1A (pΔE1A is used as prefix for the derived vectors in FIG. 1). Vector pΔE1A-N/B (FIG. 1b) was obtained by inserting an 8.3 kb NheI/Bst1107 I fragment from pPAM3, (Miller A D, et al. *Mol Cell Biol* 1986; 6: 2895–2902.) which contains the MLV left-side LTR, gagpol/env genes without packaging signal, and a polyadenylation signal, into XbaI/EcoRV site of vector pΔE1Asp1A (Microbix Biosystems Inc., Toronto, Canada).

Vector pΔE1A-N/H (Ad-N/H-1 in FIG. 1c) was constructed by inserting, a 7.9-kb NheI/HpaI fragment from pPAM3, which contains MLV LTR, and gagpol/env genes without polyA signal, into the EcoRV site of pΔE1Asp1A.

Vector pΔE1A-gp (Ad-gp2 in FIG. 1d) contains MLV gag-pol genes derived from pΔE1A-N/B in which an EcoRI fragment at the 3'-end containing part of the MLV env was deleted.

Vector pΔE1A-env (Ad-env in FIG. 1e) was produced as follows an XbaI site in the left LTR of pPAM3 was eliminated by partial XbaI digestion and Klenow fill-in. The resulting plasmid was digested with PvuI/XbaI, filled-in with Klenow, and the vector was religated. These steps eliminated most of the gag-pol genes. The resulting vector was then cut with NehI/HpaI, and the 4.66 kb fragment, containing MLV env, was inserted into EcoRV site of pΔE1Asp1A.

Transfection of 293-β Cells

293-β cells (described below) were transfected with pPAM3 and pΔE1A-N/H by calcium phosphate transfection method (Graham, F L, van der Eb A J. *Virology* 1973, 52: 456–467.) using a commercial kit from Promega (Perfection Mammalian Transfection System, Promega Co., Madison, Wis., USA). Cells were grown 48 h after transfection, and the supernatants were then recovered. filtered through a 0.45 μm filter, and used to infect NIH 3T3 cells in 6-well culture dishes in the presence of 8 μg/ml polybrene. The infected 3T3 cells were trypsinized 24 h later, and transferred to a 10-cm cell culture dishes with neomycin selection (0.75 mg/ml active G418, from Mediatech, Inc., Herndon, Va., USA). Colonies were grown in 7 to 10 days and were stained with crystal violet (0.1% in 20% ethanol) before being counted.

Transduction of cells with retroviral vectors containing neoR gene

MLV-based vectors were either transfected into an intermediate ecotropic packaging cell line GP+E-86 (Markowitz D, et al. *J Virol* 1988; 62: 1120–1124. Markowitz D, et al. *Ann NY Acad Sci* 1990; 612: 407–414.) using either calcium phosphate transfection as described above or lipofectamine transfection (Life Technologies, Inc., GibcoBRL, Gaithersburg, Md., USA) and resultant virus used to infect an amphotrophic packaging cell line PA317, (Miller A D, et al. *Mol Cell Biol* 1986; 6: 2895–2902.) or directly transfected into PA317. The three vectors used were as follows: vector pLN which contains neoR, (Miller A D, et al. *Methods Enzymol* 1993; 217: 581–599.) vector pLNPOZ which contains neoR and lac z, (Adam M A, et al. *J Virol* 1991; 65: 4985–4990.) and vector pLNCX-β. The latter was constructed by inserting a 3.7 kb HindIII/BamHI fragment containing the lac-Z gene from pCH110 (Pharmacia Biotech, Piscataway, N.J., USA) into the HindIII site of pLNCX. (Miller A D, et al. *Methods Enzymol* 1993; 217: 581–599.) The resulting producer cells from separate transfection of the three vectors are called PA317-LN, PA317-LNPOZ and PA317-β, respectively. These producer cells were then colony purified, with resulting titers ranging from $10^5$ to $10^7$ cfu/ml. All of these cell lines were free of replication-competent virus, as determined by marker-rescue assay. (Miller A D, ET AL. *Methods Enzymol* 1993; 217: 581–599.) Culture supernatants were used to transduce NIH 3T3, Hela, H9, and 293 cells. Neomycin-resistant cells were selected by neomycin analog G418 (0.75 mg/ml active). Cloned cells of 3T3-LN, 3T3-LNPOZ, Hela-LN, and 293-β were thus obtained (nomenclature: cell name-MLV vector). To characterize the market gene-containing cell lines, between 20 and 30 colonies of each of 3T3-LN-3T3-LNPOZ, and Hela-LN clones were tested. These clones were infected with an equal amount of recombinant adenovirus Ad-N/H-1 to rescue the marker gene, and the supernatants of the culture medium were titered on 3T3 cells. The resulting titers showed that about 20 to 30% of the original clones produced high titers in their supernatants after infection with Ad-N/H-1. The high titer clones were then used for further testing. H9-LN is an uncloned neoR-containing cell pool. All these cells were free of replication-competent virus, as judged by the absence of neoR phenotype in 3T3 cells infected with the culture supernatants.

Recombinant adenovirus construction

To obtain recombinant adenoviruses, each of the 4 vectors was co-transfected with either pBHG11 or pBHG10 (Bett AJ. et al. *Proc Natl Acad Sci USA* 1994, 91: 8801–8806.) into 293 cells by calcium phosphate method basically as described. (Graham F L, et al. In: Murray EJ (ed.) *Methods in Molecular Biology*, Vol. 7 Gene Transfer and Expression Protocols, Humana Press, Inc., Clifton, N.J., 1991, pp 109–128. Hitt M, et al. In: *Cell Biology: A Laboratory Handhook*, Academic Press, Ny, 1994, pp 479–490.) Briefly, 293 cells were split into 60-mm culture dishes the day before transfection in a density that would result in 70–80% confluency on the day of transfection Adenovirus vectors were transfected into 293 cells by calcium phosphate method (Graham, F L, et al. AJ. *Virology* 1973;. 52: 456–467.) using a commriercial kit (Promega) according to manufacture's instructions. Six to ten μg of each DNA was used for cotransfection. Transfected 293 cells were incubated overnight in a $CO_2$ incubator and then the culture media were aspirated and replaced with fresh media of 5% horse serum (HS)/MEM. Cells were transferred to 10-cm dishes when confluent, and cytopathic effect was observable in 1 to 2 weeks. The resulting recombinant viruses were separately plaque-purified, expanded in 293 cells and then purified in a CsCl gradient. (Graham F L, et al. In: Murray EJ (ed.) *Methods in Molecular Biology*, Vol. 7: Gene Transfer and Expression Protocols, Humana Press, Inc., Clifton, N.J., 1991, pp 109–128. Hitt M, et al. In: *Cell Biology. A Laboratory Handbook*, Academic Press, Ny, 1994, pp 479–490.) The CsCl gradient-purified adenoviral vectors were used for delivering MLV gagpol and env genes. In addition, DNA was extracted and purified from the CsCl-purified viruses and the constructs were verified by restriction digestion and nucleotide sequencing.

Western blot analysis and RT assay

Cells were detached from plates with EDTA and dissolved in sample buffer in the presence of β-mercaptoethanol at a concentration of 0.1 mg cell weight (wet) per microliter. This resulted in protein concentration of approximately 1 mg/ml. Five microliters of the sample was applied to 10% SDS-polyacrylamide gel (Novex pre-case gels in Tricine buffer, from Novex, San Diego, Calif., USA) and blotted to PVDF membrane according to standard procedures. The membrane was then probed with pig anti-amphotrophic MLV serum (Quality Biotech, Camden, N.J., USA), washed, and then reacted with rabbit anti-pig IgG-peroxidase conjugated (Sigma Chemical, St Louis, Mo., USA) The blot was developed with an enhanced chemiluminescent substrate from PIERCE (Rockford, Ill., USA) according to manufacturer's instructions. RT assay was performed using a commercial kit (Boehringer Mannheim, Indianapolis, Ind., USA), which is based on a calorimetric enzyme immunoassay method. A buffer system adapted for MLV RT assay was used and the amount of RT was calibrated according to HIV RT standard.

Generation of retroviral producer cells by retroviral and adenoviral infection

Hela or 3T3 cells were grown in DMEM/10% FCS and then plated in 6-well plates with $2.4 \times 10^5$ cells/well at day one to reach about 40–60% confluence at day two. All culture media containing the MLV virus-like particles were centrifuged at 1,500 rpm for 10 min in a Beckman GPR centrifuge. To avoid possible contamination from producer cells, only the top layers of the centrifuiged supernatant were used for infection. Frozen supernatants were thawed and centrifuged only, while fresh supernatants were centrifuged and then filtered through 0.45 μm filters before being used for infection. The cells were separately infected with the supernatants from MLV producer cells PA317-LN or PA317-LNPOZ in the presence of 8 μg/ml polybrene and adenoviral vectors Ad-N/H-1, Ad-gp2, and Ad-env3. Cells were washed with medium three times after infection to completely remove residual retroviral particles and then cultured for two additional days. Supernatants were then harvested and frozen at −70° C. for titer analysis. Titers were determined on 3T3 cells according to standard clonogenic assay (Miller A D, et al. *Methods Enzymol* 1993; 217: 581–599.) procedure with G418 selection. Briefly, 3T3 cells were plated in 6-well plates as described above the day before infection. After infection with different dilutions of supernatants in the presence of polybrene, the cells were incubated in a $CO_2$-incubator for 24 h before being transferred into 10-cm dishes and selected with G418 (0.75 mg/ml active G418). Selection media were changed after each period of 2 to 3 days, and colonies were stained with either crystal violet (0.1% in 20% ethanol) or X-gal before counting. Marker rescue assays (Miller A D, et al. *Methods Enzymol* 1993; 217: 581–599.) were performed for these supernatants, using 3T3-LN clones as templates and no replication-competent virus was found in all of the supernatants tested. Controls include 3T3 and Hela cells infected with supernatants from either PA317-LN or PA317-LNPOZ alone, or infected with adenoviral vectors alone. Additional controls include infection of 3T3-LN, 3T3-LNPOZ and Hela-LN clones with either Ad-gp2 or Ad-env3 alone. All of these controls produced no count when titered on 3T3 cells.

Genomic analysis of NIH 3T3-pLN cells

Three different cells were used to analyze the genomic integration patterns of retroviral vectors. NIH 3T3 cells were used as negative controls. A clone of NIH-pLN, NIH-pLN-1, was used as single-site integration cells. A population of NIH 3T3 infected with retroviral vector carrying pLN, NIH-pLN-pool, was used as multiple-integration cells. Genomic DNA was purified from cells ($3 \times 10^6$) using a commercial kit (Wizard Genomic DNA Purification System, Promega) according to manufacturer's instructions. The DNA (7 μg) from these three cell lines was digested with Bam HI, which is not cut in pLN gene, and then separated on 1% agarose gels. The gels were cut into 9 equal sections from 3 to 20 kb, and about 5 μl from each section was used as templates for PCR amplifications. Two internal primers of pLN were used for the PCR: forward primer 5'-CCCGATTCGCAGCGCATCGCCTTCTATCGC (SEQ ID NO. 1); and reverse primer 5'-GCAGAGGAGACCCTCCCAAG (SEQ ID NO. 2). PCR was performed with a "touch-down" method, with separation for 40 seconds at 94° C., extension for 60 seconds at 72° C., and various annealing temperatures of 55° C., 53° C., 50° C. for 5 cycles each followed by 48° C., 46° C., 44° C. for 10 cycles each. A 0.67 kb band is expected from the PCR, which showed in some sections of NIH-pLN-1 and NIH-pLN-pool, but not in NIH 3T3 DNA.

Isolation and Infection of PBMCs

Peripheral blood mononuclear cells (PBMCs) were isolated from healthy donors by Ficoll-Hypaque density-gradient centrifugation and cultured initially in RPMI 1640 media containing 20% FCS in the presence of phytohemagglutinin (PHA-P, from Sigma, 5 μg/ml). Continuous culture of the cells was done in the same media with interleukin-2 (human recombinant IL-2 from GibcoBRL, 200 u/ml). (Gartner S, et al. In: Aldovini A, and Walker B D (eds) *Techniques in HIV Research*, Stockton Press, 1990, pp 53–70.) PBMCs ($9 \times 10^6$ in 5 ml) were infected with 5 ml of supernatant from PA317-LNPOZ ($5.8 \times 10^6$ cfu/ml) in the presence of 8 μg/ml polybrene for 4 h. Cells were washed three times with PBS, and then resuspended in 6 ml of growth medium with IL-2. Cells were seeded into a 24-well plate with 1 ml aliquots, and infected with Ad-N/H-1 with MOI of 0, 5, 10, 20, 50, and 100. Supernatants from the infections were harvested two days later, and titered on NIH 3T3 cells as described above.

Example 1

Construction and Functional Tests of Adenoviral Vectors

The four different fragments of MLV genes which were cloned separately into adenoviral vector pΔE1Asp1A (pΔE1A is used as prefix for the derived vectors in FIG. 1) were tested for their functionality. Vector pΔE1A-N/H, which contains all 3 MLV structural genes, was transfected by calcium phosphate coprecipitation method into 293 β cells, which contain an integrated marker β-galactosidase gene originally transduced from a retroviral vector. The expression of MLV structural genes would rescue the marker gene, and package it into the resulting retroviral vectors. In parallel experiments, the parent vector (pΔE1A) and the vector containing the insert, pPAM3 (Miller A D, et al. *Mol Cell Biol* 1986; 6: 2895–2902) (FIG. 1) were transfected into the same cells as negative and positive controls, respectively. The supernatants of the cells were used to infect NIH TK-cells (Wei C M, et al. *J Virol* 1981; 39: 935–944) (NIH 3T3 or 3T3 cells)), which were stained with X-gal. The results, presented in Table 1, clearly showed that when transfected into 293-β cells, pΔE1A-N/H can rescue the β-gal gene in a retrovirus vector.

TABLE 1

Transfection of 293-β cells with MLB genes.

| | Titer (cfu)* |
|---|---|
| pΔE1A | 0 |
| pΔE1A-N/H-1 | 61 ± 13 |
| PpaM3 | 180 ± 58 |

*Titers are expressed as colony forming unit (cfu) per ml and each set of data represents 5 independent experiments.

Construction of recombinant adenoviruses based on these vectors was then attempted. The MLV insert in vector pΔE1A-N/B is near the size limit of 8.3 kb for recombination with pBHG11 in 293 cells. (Bett A J, et al. *J Virol* 1993; 67: 5911–5921, Bett A J, et al. *Proc Natl Acad Sci USA* 1994; 91: 8801–8806) Efforts to obtain recombinants using this system were fruitless. Successful recombinant adenovirus derived from pΔE1A-H/H (7.9 kb, at maximal insert size for rescue into BHG10 (Bett A J, et al. *Proc Natl Acad Sci USA* 1994; 91: 8801–8806)) and pBHG10 was obtained after hundreds of transfection attempts. The resulting recombinant adenovirus vector Ad-N/H-1 has the capacity to deliver all MLV gag-pol-env genes. For comparison, recombinants between pBHG10 and either pΔE1A-gp or pΔE1A-env wer also obtained. These recombinant vectors separately deliver MLV gag-pol-env genes (Ad-gp2) and env gene (Ad-env3).

Example 2

Infection of NIH3T3 Cells with Recombinant Adenoviral Vectors Results in the Expression of MLV Structural Genes The expression of MLV structural gene products in 3T3 cells was monitored by Western Blot, using an anti-MLV antiserum, after infection with CsCl purified recombinant adenoviruses Ad-N/H-1, Ad-gp2, and Ad-env3 Three known MLV protein bands, (Felsenstein K M, et al. *J Viral* 1988; 62: 2179–2182; Miller A D, et al. *J Virol* 1984; 49: 214–222) gp80 (env), p65 (gag) and p30 (gag), whose positions in Western blot are marked by a retroviral packaging cell line PA317 (Miller A D, et al. *Mol Cell Biol* 1986; 6: 2895–2902), are clearly visible over the background bands from the untransfected cells. Cells infected with adenoviral vector Ad-N/H-1 (contains MLV-gagpol/env genes) produced all 3 major MLV protein bands whose relative intensities correlate with the vector dosage and the time of infection.

SDS-PAGE/Western blot analysis of NIH 3T3 cells infected with adenoviral vectors was performed, comparing PA317; untransfectedNIH 3T3 cells; NIH 3T3 cells infected with Ad-N/H-1 at a virus/cell ratio of 1:1 and 24 h; NIH 3T3 cells infected with Ad-N/H-1 at a virus/cell ratio of 5:1 and 24 h, NIH 3T3 cells infected with Ad-N/H-1 at a virus/cell ratio of 5:1 and 48 h NIH 3T3 cells infected with Ad-N/H-1 at a virus/cell ratio of 10:1 and 24 h; NIH 3T3 cells infected with Ad-gp2 (48 h); NIH 3T3 cells infected with Ad-env3 (48 h); and NIH 3T3 cells infected with both Ad-gp2 and Ad-env3 (48 h). Cells receiving only gag-pol genes (Ad-gp2) produced only the expected proteins p65 and p30. Likewise infection of Ad-env3 produced only gp80. Coinfection of Ad-gp2 and Ad-env3 produced all 3 bands, Reverse transcriptase (RT) assays were performed to assess the virus production in the supernatants. The results showed that while the supernatants from PA317 clones contains 0.25 ng/ml RT, the supernatant from Ad-N/H-1 and Ad-gp2 infected cells contain RT from 0.02 to 8 ng/ml depending on the dose and duration of the adenovirus infection. These results clearly demonstrate that the transfer of MLV genes by the adenoviral vectors resulted in the proper expression of MLV proteins for the packaging of MLV particles.

Example 3

Cotransduction of Cells with Retroviral and Adenoviral Vectors to Generate New Producer Cells In order to transduce cloned cells into producer cells, the marker genes neoR (from pLN) and neoR+lac z (from pLNPOZ) were first transduced into NIH 3T3 and Hela cells, and high titer clones were selected. When different amounts of recombinant adenovirus Ad-N/H-1 were used to infect both mouse fibroblast cells line NIH 3T3-LN clones and human T-cell line H9-LN, (Popovic M, et al. *Science* 1984; 224: 497–500.) the resulting titers correlate with the amount of adenoviral vector used at dosages below saturation (Table 2).

TABLE 2

Rescue of retroviral vectors with different amounts of Ad-N/H-1.

| Clones | 0[a] | 1[a] | 2[a] |
|---|---|---|---|
| 3T3-LN-7[b] | 0 | $1.1 \times 10^3$ | $2.0 \times 10^3$ |
| 3T3-LN-21[b] | 0 | $7.4 \times 10^3$ | $1.4 \times 10^3$ |
| 3T3-LNPOZ-16[c] | 0 | $8.0 \times 10^3$ | $1.7 \times 10^4$ |

TABLE 2-continued

Rescue of retroviral vectors with different amounts of Ad-N/H-1.

| Clones | 0[a] | 1[a] | 2[a] |
|---|---|---|---|
| H9-LN[d] | 0 | $4.0 \times 10^2$ | $7.4 \times 10^2$ |

[a]These numbers represent only the relative amount of Ad-N/H-1 used to infect the cells.
[b]3T3-LN were plated in 6-well plates and infected with 0, 1, and 2 ml of supernatants from Ad-N/H-1 infected 293 cells. The resulting supernatants were then titered on NIH 3T3.
[c]3T3 cells in 6-well plates were infected with CsCl purified Ad-N/H-1 with MOI of 0, 7 and 14 respectively. The resulting supernatants were then titered on NIH 3T3 cells.
[d]H9-LN were infected with Ad-N/H-1 with MOI of 0, 140, and 280, respectively. The resulting supernatants were then titered on NIH 3T3 cells.
All the above titers are described as cfu/ml.

Table 2 also shows that the titers are zero without recombinant retrovirus. These results clearly show that the 'naive cells' were transduced into the second generation producer cells by a combination of retroviral and adenoviral vectors.

The titers generated from the producer cells resulting from different procedures were investigated. Several retroviral vector transduced and cloned cell lines, NIH 3T3-LN, NIH 3T3-LNPOZ, and Hela-LN, which contain marker genes, were transduced separately with Ad-N/H-1 or Ad-gp2+Ad-env3 using high multiplicity of infection (MOI), ranging from 5:1 to 10:1 (Table 3).

TABLE 3

Titers of different LN and LNPOZ clones infected with Ad-N/H-1 and Ad-gp2 plus Ad-env3.

| Clones | Ad-N/H-1 ($\times 10^5$ cfu/ml)[a] | Ad-gp2 + Ad-env3 ($\times 10^4$ cfu/ml) |
|---|---|---|
| 3T3-LN-1 | 1.2 ± 0.4 | 1.8 ± 0.5 |
| 3T3-LN-21 | 0.31 ± 0.38 | 0.74 ± 0.63 |
| 3T3-LN-22 | 3.3 ± 0.6 | 0.13[b] |
| 3T3-LNPOZ-5 | 1.4 ± 0.8 | 0.44[b] |
| 3T3-LNPOZ-16 | 0.96 ± 0.24 | ND[c] |
| Hela-LN-7 | 0.14 ± 0.09 | 0.23[b] |
| Hela-LN-13 | 0.088 ± 0.028 | 0.24 ± 0.16 |
| Hela-LN-21 | 0.085 ± 0.023 | 0.13 ± 0.03 |

NIH3T3-LN, NIH3T3-LNPOZ and Hela-LN clones were infected with either Ad-NIH-1 or Ad-gp2 plus Ad-env-3. Supernatants from the resulting infections were then used to infect. NIH3T3 cells and selected with G418. Tile neomycin-resistant colonies were then counted and expressed as cfu per ml.

[a]Results are mean±standard deviation for three determinations.
[b]Single determination.
[c]ND: not determined.

Table 3 shows that the titers for the 3T3 clones ranged from $3 \times 10^4$ to $3 \times 10^5$ cfu/ml and for HeLa clones ranged from $8 \times 10^3$ to $1 \times 10^4$ cfu/ml. Control cells without adenoviral vector infection or with either Ad-gp2 or Ad-env3 alone resulted in zero titer. The sensitivity of HeLa cells to the cytopathic effect of Ad-N/H-1 may account for the titer being lower than that from Ad-N/H-1, possibly because of the uneven transfer and expression of gp2 and env3 genes in individual producer cells. In separate experiments, 3T3, H9 and Hela cells were transduced with retroviral vector LN and selected for neoR. The resulting uncloned cell populations (pools) were infected with Ad-N/H-1 and their titers determined (Table 4).

TABLE 4

Titers of retroviral infected cell pools infected with Ad-N/H-1.

| Cell Pools | Ad-N/H-1 (× $10^5$ cfu/ml) |
|---|---|
| 3T3-LN-1 | 2.6 ± 1.1[a] |
| H9-LN | 0.0074[b] |
| Hela-LN | 0.0011[b] |

Cells (3T3, H9, and Hela) were infected with supernatant from PA317-LN, selected with G418, and then infected with Ad-N/H-1. The resulting supernatants were titered on 3T3 cells as described in Methods.
[a]Mean ± standard deviation for three determinations.
[b]Single determination.

Values for some of these titers were expectedly lower than those from the cloned cells (Table 3). This was likely due to the hetrogeneous integration and expression of the retroviral vectors.

The integration of retroviral gene into host genome was analyzed by the identification of pLN originated sequence in cellular DNA. Genomic DNA from transduced cells was digested from Bam HI, a site absent in LN gene, and size-separated by agarose gel electrophoresis. The location of LN gene was identified by polymerase chain reaction (PCR) using the cut gel slices as templates. DNA from cloned 3T3 cells transduced with pLN (NIH-pLH-1) showed a single LN positive band at 9 kb. As expected, an uncloned pool of NIH-LN showed a broad range of LN positive bands ranging from 6 to 9 kb. No positive band was detected in the untransduced 3T3 cells. These results clearly showed the single-site integration of the NIH-pLN-1 and the hetrogeneous integration of the NIH-pLN-pool Attempts were made to convert human peripheral blood mononuclear cells (PBMCs) into producer cells. PMBCs were simultaneously superinfected with both retroviral and adenoviral vectors and then titered without selection With this simplified procedure, the titers were predictably lower for all three cells The titer of PBMCs were about 100 to 200 cfu/ml, which is similar to that produced by NIH 3T3 (320 cfu/ml) nd HeLa (21 cfu/ml) cells. These data suggest that the current vectors have the potential to achieve acceptable titers for the second generation producer cells originating from different cell types. These results also demonstrate that human primary cells can be converted into producer cells by superinfection of retroviral and adenoviral vectors.

The decay of titer in the culture supernatants of the new producer cells was analyzed during continued cell culture. After three splits of cultured cells at two-day intervals, the titers decreased by about tenfold (Table 5).

TABLE 5

Titers of the new producer cells with long term culture in the absence of selection.

| Clones | Vector:Cell Ratio | Sup-I (cfu/ml)[a] | Sup-II (cfu/ml) | Sup-III (cfu/ml) |
|---|---|---|---|---|
| Hela-LN-7 | 2:1 | 5.5 × $10^3$ | 1.6 × $10^3$ | 4.9 × $10^2$ |
| Hela-LN-7 | 5:1 | 2.5 × $10^4$ | 2.1 × $10^3$ | 5.2 × $10^2$ |
| Hela-LN-13 | 2:1 | 6.6 × $10^2$ | 6.5 × $10^2$ | ND[b] |
| Hela-LN-13 | 5:1 | 5.9 × $10^3$ | 2.7 × $10^3$ | ND |
| Hela-LN-21 | 2:1 | 1.4 × $10^3$ | 1.6 × $10^3$ | ND |
| Hela-LN-21 | 5:1 | 8.1 × $10^3$ | 1.0 × $10^3$ | ND |
| Hela-LN-22 | 5:1 | 1.7 × $10^3$ | 3.9 × $10^3$ | 3.9 × 10 |
| 3T3-LNPOZ-5 | 5:1 | 2.3 × $10^5$ | 6.5 × $10^2$ | ND |

Retroviral vector-containing cells were cultured in 6-well plates and infected with Ad-N/H-1 as described in Methods. Supernatants were collected 2 days after the infection (Sup-I), and cells were trypsinized and transferred to 10-cm plates and culture continued without selection. the resulting supernatants were collected again after 2 days (Sup-II), and cells were split and cultured again. The final supernatants were collected after another 2 days (Sup-III).
[a]All titers in this table are single determinations.
[b]D: not determined.

The results demonstrate that reasonable titers can be maintained over a short duration even though adenovirus transduction does not result in the integration of the MLV genes into the host chromosomes.

Example 4

Construction of Safer AdenoviRal/MLV System

Figure 2:
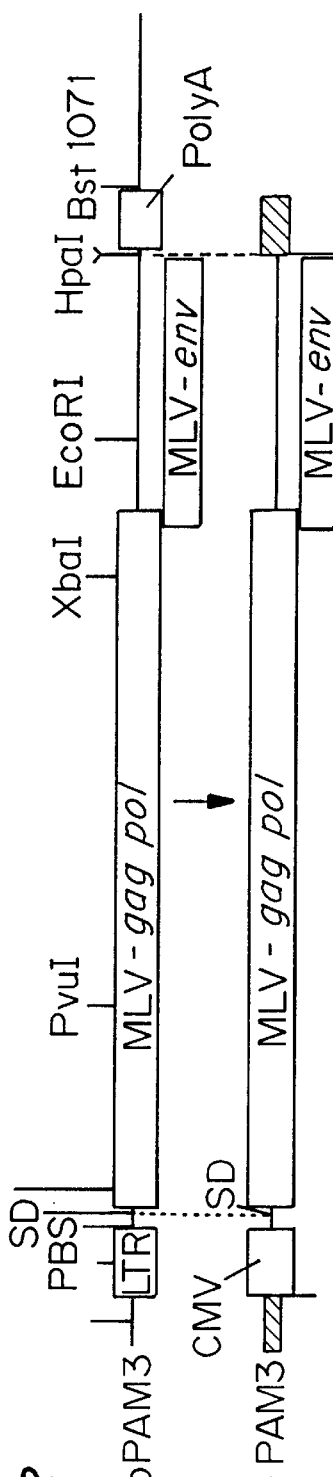
FIG. 2 are schematics of the construction of vector pCA3-PAM3, showing elimination of the LTR and PBS site while retaining the SD site in vector pCA3-PAM3. The adenovirus vector pCA3 is drawn in the reverse direction. 1 u 9.8 u in the figure represent the map unit of the adenovirus.

In order to improve the safety of the adenoviral vector Ad-N/H-3, which delivers MLV gagpol/env genes, the 5'-LTR down to the PBS (primer binding site) in pPAM3 was eliminated and replaced with a CMV promotor, which has been shown to be able to properly promote the expression of the down stream gagpol/env genes (FIG. 2).
Experimental Procedures In order to eliminate the 5'-LTR and the PBS site, but retain the splicing donor (SD) site in vector pPAM3 (FIG. 2), PCR primers were designed to amplify a 230 bp fragment from the SD to the PstI site. The 5'-primer (CAM3P1) is: 5'-GTTAAC CAG GGA CCA CCG ACC CAC CAC CGG GAG GTA AGC TGG GtT GCA GCA TCG-3' (SEQ ID NO. 3), where the italic letters represent an installed HpaI site and the small letter t is a mutation changed from C that eliminated the 5' side PstI site. The 3'-primer (CAM3P2) is: 5'-CTGCAG AGC AGA AGG TAA CCC-3' (SEQ ID NO. 4), where the italic letters are the original PstI site shown in FIG. 2. The 230 bp PCR product was cut with HpaI/PstI, and cloned into the EcoRV/PstI site of pBlue KS (Stratagen). A 240 bp Hind III/PstI fragment was then recovered from the resulting vector, and together with a 7.0 kb PstI/HpaI fragment from pPAM3 (FIG. 2), were cloned into the HindIII/EcoRV site of pCA3 (Microbix). This results in the vector pCA3-PAM3 also shown in FIG. 2.

Example 5

Constiuction of an Adenovirus/HIV System

Figure 3A:
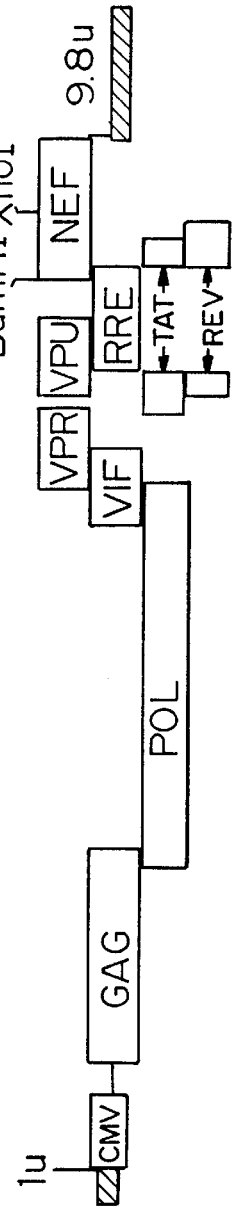
FIGS. 3A, 3B and 3C are schematics of the construction of adenovirus vectors that deliver HIV-gagpol and marker genes.
Figure 3B:
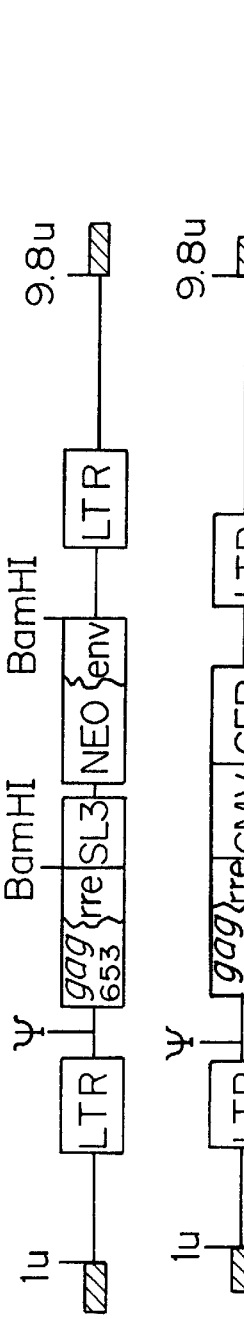
Figure 3C:
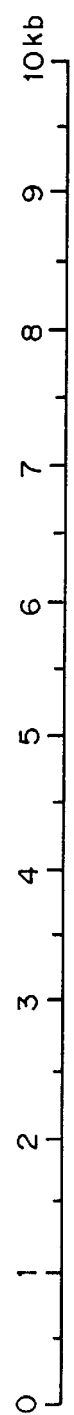

This system is conceptually the same as that for the adenovirus/MLV system of Examples 1–4. However, the gene delivery vectors are HIV based instead of MLV based. The construction of three vectors are described below and with reference to FIGS. 3A, 3B and 3C. FIGS. 3A, 3B and 3C show the structure of three adenovirus vectors for delivering HIV-1 gagpol genes and marker genes in the lentivirus construct. For constructing HIV-gagpol genes, a vector pCMVΔR8.2 from Dr. Inder Verma of The Salk Institute for Biological Studies. One of the three NotI sites, which is upstream of RRE, was eliminated by partial NotI digestion, Klenow fill-in, and ligation. The resulting vector was cut with NotI, and a 7.4 kb fragment, which contains gagpol, rev, Vif, Vpr, Vpu, RRE, and Nef genes, was Klenow filled-in, and cloned into the EcoRV site of pCA14 (Microbix Biosystems Inc., Toronto, Canada). The resulting vector, pCA14ΔR8.2 (FIG. 3A), is similar to the original pCMVΔR8.2 in that the HIV structural and accessory genes are under the control of a CMV promotor. The total insert size of pCA14ΔR8.2, starting from the CMV promotor to the end of the Nef gene, is about 7.8 kb, which is below the limit of 7.9 kb for recombination with pBHG10. Vector pCA14ΔR8.2 was co-transfected with pBHG10 into 293 cells using calcium phosphate method as described (1), and the recombinant virus, Ad-CA14ΔR8.2, has been obtained and is in the process of plaque-purification and characterization.

Vector pΔE1A-V653-RSN (FIG. 2B), an adenovirus vector, was designed to deliver a marker (NEO) gene in the HIV genomic construct. The parent plasmid v653-RSN was obtained from Dr. Joseph Sodroski. Plasmid v653-RSN was cut with ClaI, then partially cut with NdeI. The resulting 7.6-kb fragment was recovered and filled-in with Klenow before it was cloned into the EcoRV site of pΔE1sp1A (Microbix) to form the plasmid pΔE1A-v653-RSN. The insert size (7.6 kb) was well below the limit of 7.09 kb for recombination with pBHG10. Vector pΔE1A-v653-RSN was co-transfected into 293 cells with PBHG10 and the recombinant virus, Ad-v653-RSN, obtained and plaque purified and characterized. Vector pΔE1A-V653-GFP (FIG. 3C), which delivers the green fluorescent protein (GFP) as a marker gene, was constructed by first replacing the BamHI fragment of the SL3-NEO in v653-RSN with a BglII/BamHI fragment of CMV-GFP from pQBI-25 (Quantum Biotechnologies Inc. Montreal (Quebec) Canada H3H 1J9) to obtain plasmid v653-GFP, which was then cut with NdeI/ClaI and cloned into pΔE1A. The resulting vector pΔE1A-V653-GFP was transfected into NIH 3T3 cells with Lipofectmine Plus (Life Technologies, GIBCO-BRL), and strongy fluorescence observed in the transfected cells. Thus the CMV-GFP is functional in this vector.

Example 6

Cancer Gene Therapy (i) Cloning and Retroviral Delivery of tk Gene.

Figure 4A:
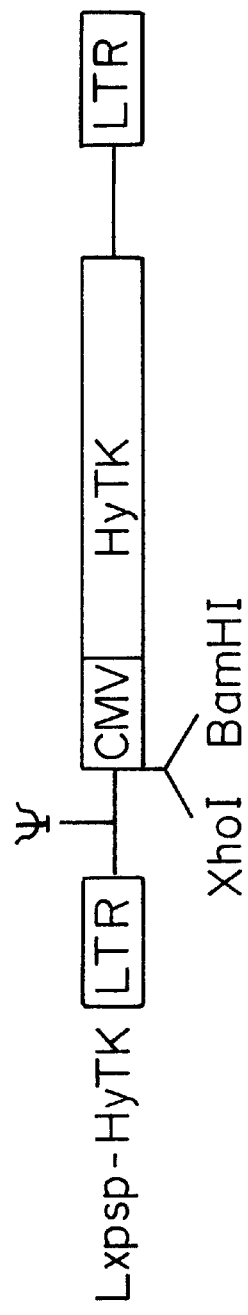
FIGS. 4A and 4B are schematics of constructs of retroviral vectors for delivering the TK and vhs genes.
Figure 4B:
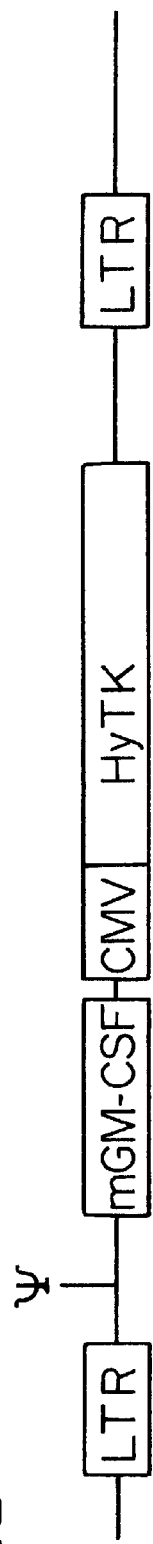

An MLV-based vector, pLXSN, was digested with EcoR I, and then treated with Klenow following ligation to eliminate the EcoR I site. The resulting vector was cut with Bam HI/Nco I, filled-in with Kienow, and religated to eliminate most of the Neo sequence in the original vector. The new vector called pLX was cut with Xho I/Bam HI. An Xho I/Bgl II polylinker fragment from psp73 (Promega) was then cloned into the Xho I/Bam HI cut of pLX. The resulting vector is called Lxpsp, which contains the MLV-LTR plus a polylinker site for cloning. A 2.9 kb Xho I/Bgl II fragment from vector tgCMV/HyTK was then cloned into the EcoR I site of Lxpsp, resulting in Lxpsp-HyTK (FIG. 4A), which contains a hygromycin B-thymidine kinase fusion gene under the control of a CMV promotor in an MLV vector. Lxpsp-HyTK was transfected into an ecotropic packaging cell line GP+E-86 by calcium phosphate transfection, and the supernatant used to infect an amphotropic packaging cell line PA317. High-titer clones of PA317-HyTK were then obtained by colony selection and titration. A dual-expression vector pLmGM-CSF-HyTK (FIG. 4B) was cloned by inserting a 0.45 kb Sal I/Bam HI mGM-CSF (mouse granulocyte-monocyte colony stimulating factor) gene into the Xho I/Bam HI site of Lxpsp-HyTK. The mGM-CSF gene is obtained from vector pNGVL1-mGM-CSF, which was obtained from the National Gene Vector Laboratory (NGVL) plasmid repository at the University of Michigan. This vector is an "enhanced" version of the HyTK vector, due to the immune-stimulating effect of GM-CSF.

PA317-HyTK cells were cloned, and the high-titer clones selected. The results showed that the parental cell lines, NIH-TK⁻, K-Balb, and 80TIB, are all resistant to GCV and can only be killed at 1 mM of GCV concentration. The high titer tk-containing clones of these cells, which include HyTK and HyTK-mGM-CSF, are sensitive to GCV and can be killed at 10 □M of GCV concentration.

(ii) Animal Experiments.

Balb/c mice were used as animal models and the tumor cell line K-Balb was used as tumor inoculation cells. For tumor inoculation, each mouse was injected with tumor cells only ($2 \times 10^6$ tumor cells/inoculation) in the left flank and tumor ($2 \times 10^6$ cells) plus packaging cells ($8^{33\ 105}$ cells) in the right flank. Tumors were grown to almost full size at day twelve, and ganciclovir (150 mg/ml, twice daily for five days) was injected intraperitoneally.

Examination of the control mouse (left), which was inoculated on the left side with K-Balb cells and on the right side with K-Balb+PA317 packaging cells, revealed that the tumor size at the two sites are about the same after treatment. However, for the test mouse which was inoculated with K-Balb cells on the left side and with K-Balb+PA371-HyTK on the right side, the right-side tumor significantly shrank after treatment. These initial experiments showed that the in vivo delivery of the HSV-TK gene sensitized tumor cells to be ablated by the drug ganciclovir.

The teachings of the references cited herein are specifically incorporated herein. Modifications and variations of the present invention will be obvious to those skilled in the art from the foregoing detailed description and are intended to be encompassed by the following claims.

What is claimed is:

1. A method of making a producer cell that delivers a marker gene or therapeutic gene to a target cell, wherein the producer cell is a human primary cell, comprising the steps:
   using a retroviral vector to deliver a marker or therapeutic gene to the human primary cell; and
   using a single adenoviral-based vector to deliver the gag, pol and env structural genes to the human primary cell, thereby making a producer cell.

2. The method of claim 1, wherein the retroviral vector is a Moloney murine leukemia virus (MLV) based vector to deliver a marker or therapeutic gene to the human primary cell.

3. The method of claim 1, wherein the retroviral vector is a lentivirus.

4. The method of claim 1 wherein the gag, pol and env structural genes are from Moloney murine leukemia virus.

5. The method of claim 3 wherein the lentivirus is human immunodeficiency virus.

6. The method of claim 3, wherein the structural gag, pol and env structural genes are from human immunodeficiency virus-1.

7. A producer cell that delivers a marker gene or therapeutic gene to a target cell, wherein the producer cell is a human primary cell transfected with a first retroviral vector delivering a marker or therapeutic gene to the human primary cell; and a second single adenoviral-based vector delivering the gag, pol and env structural genes to the human primary cell.

8. A system for making a producer cell that delivers a marker gene or therapeutic gene to a target cell, wherein the producer cell is a human primary cell, the system comprising:

a first retroviral vector for delivering a marker or therapeutic gene to the human primary cell; and a second adenoviral-based vector for delivering the gag, pol and env structural genes to the human primary cell.

9. The system of claim 8 wherein the first retroviral vector is a Moloney murine leukemia virus (MLV) based vector to deliver a marker or therapeutic gene to the human primary cell.

10. The system of claim 8, wherein the first retroviral vector is a lentivirus.

11. The system of claim 8 wherein the gag, pol and env structural genes are from Moloney murine leukemia virus.

12. The system of claim 10 wherein the lentivirus is human immodeficiency virus.

* * * * *